United States Patent [19]

Martini

[11] 4,033,984
[45] July 5, 1977

[54] PROCESS FOR THE MANUFACTURE OF PERFLUORALKOXY-PROPIONIC ACID FLUORIDE

[75] Inventor: Thomas Martini, Neuenhain, Taunus, Germany

[73] Assignee: Hoechst Aktiengesellschaft, Frankfurt am Main, Germany

[22] Filed: July 18, 1975

[21] Appl. No.: 597,382

[30] Foreign Application Priority Data

June 20, 1974 Germany .......................... 2434992

[52] U.S. Cl. ..................... 260/340.6; 260/606.5 P
[51] Int. Cl.² ..................................... C07D 319/10
[58] Field of Search ................................ 260/340.6

[56] References Cited

UNITED STATES PATENTS 3,321,517  5/1967  Selman .......................... 260/340.6

*Primary Examiner*—Ethel G. Love
*Attorney, Agent, or Firm*—Curtis, Morris & Safford

[57] ABSTRACT

Reaction of hexafluoropropene epoxide with phosphoric acid tris-(dialkylamides) gives the new perfluoro-α-[3.6-dimethyl-1.4-dioxanyl-2-oxy]-propionic acid fluoride. By hydrolysis and decarboxylation of the acid in the presence of fluorine perfluoro-2-ethoxy-[3.6-dimethyl-1.4-dioxane] is obtained which can be used as chemically inert lubricant or heat transfer liquid.

8 Claims, 1 Drawing Figure

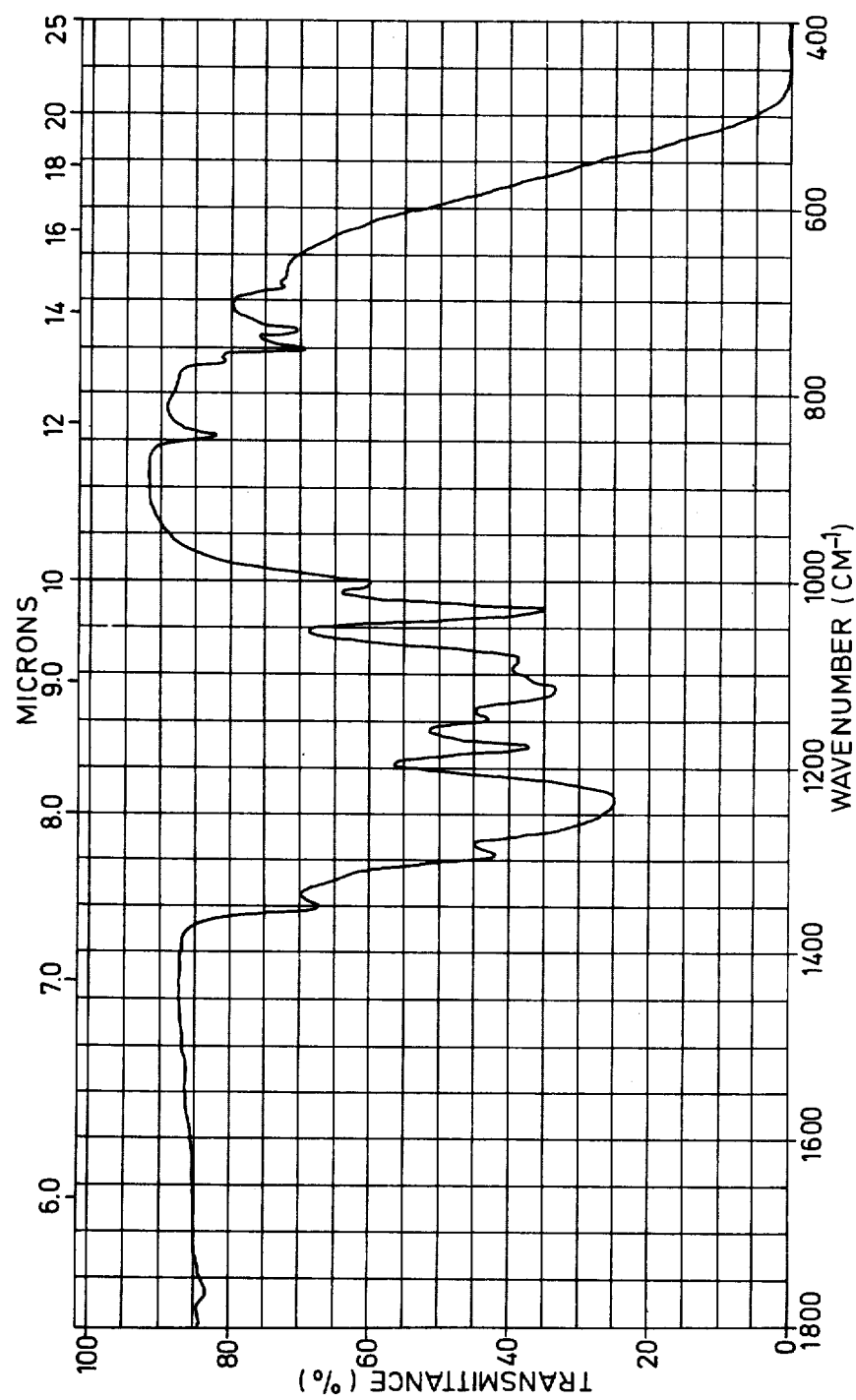

PROCESS FOR THE MANUFACTURE OF PERFLUORALKOXY-PROPIONIC ACID FLUORIDE

Perfluorated alkene epoxides such as tetrafluoroethylene epoxide or hexafluoropropene epoxide add to perfluorated carboxylic acid fluorides in the presence of catalysts such as alkali fluorides, quaternary ammonium fluorides, silver fluoride or charcoal while forming polyperfluoralkoxy carboxylic acid fluorides which are important starting products for the manufacture of high-quality lubricants. These lubricants are obtained by hydrolysis of the carboxylic acid fluorides to yield the corresponding acids and subsequent fluorinating decarboxylation which leads to saturated ethers containing one carbon atoms less. They are extremely stable chemically, even when heated, and are very resistant to great stress. On the other hand, the described reaction produces regularly a mixture of producucts having molecular weights widely diferring.

Silver nitrate is used as catalyst for successfully carrying out the selective dimerization of hexafluoropropene epoxide according to Belgian Pat. No. 751 076 while simultaneously perfluoro-α-propoxypropionic acid fluoride is produced.

According to the invention a novel perfluoralkoxypropionic acid fluoride is now obtained having the composition of $C_9F_{16}O_4$, yielding simultaneously difluorophosphoranes at almost quantitative rates.

The process according to the invention for the manufacture of perfluoralkoxypropionic acid fluoride having the composition $C_9F_{16}O_4$ and for the simultaneous manufacture of difluorophosphorane comprises that hexafluoropropene-epoxide of formula

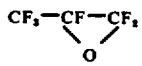 (I)

reacts with a phosphorus compound of the general formula

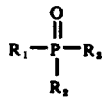 (II)

wherein $R_1$, $R_2$ and $R_3$ represent identical or different dialkylamino radicals the alkyl groups having from 1 to 4 carbon atoms, at temperatures of from −50° to +10° C.

Unless the aim is the manufacture of a special difluorophosphorane, preference is given to the use of phosphorus compounds of formula II the alkyl groups of which are identical and which have from 1 to 2 carbon atoms. Especially suitable is phosphoric acid tris-dimethyl amide, the yields obtained with phosphoric acid-tris-dialkylamides having from 2 to 4 carbon atoms per alkyl group are slightly inferior.

Generally, the process according to the invention is carried out in such a way that the phosphorus compound of formula II is charged first and hexafluoropropene epoxide introduced subsequently at the chosen reaction temperature. However, it is as well possible to introduce hexafluoropropene epoxide first and to meter in the phosphorus compound subsequently.

Hexafluoropropene epoxide may be used pure. But, hexafluoropropene under the conditions of the process according to the invention being inert, a corresponding quantity of the mixture of hexafluoropropene and hexafluoropropene epoxide which is obtained when preparing hexafluoropropene epoxide may be used as well.

A general practice is to use three moles of hexafluoropropene epoxide I per one mole of the phosphorus compound II. In order to push the reaction up to the point of complete conversion, a minor excess quantity of epoxide — up to about 10% — is advantageous. After completion of the reaction it is easy to recover non-reacted epoxide from the reaction mixture.

The speed at which the epoxide is added is of minor importance. The required quantity may be added in its liquid state and all at once. Depending on the speed of the the addition and on the reaction temperature, the reaction time varies from half an hour to 10 hours.

The reaction temperature may vary from −50° C to +10° C. A temperature of +10° C must not be surpassed, since higher temperatures induce undesirable secondary reactions. The most useful temperature range keeps below 0° C, preference is given to operational temperatures of from −40° to −25° C which permit an operation at normal pressure. Reaction temperatures above −25° C which may recommend the use of pressure devices can be interesting insofar that they allow for operating without special solvents. Particularly favorable yield rates are obtained when at −10° C hexafluoropropene epoxide is introduced at the same speed as it is consumed.

Solvents or solvent mixtures suitable for the process have to be polar, aprotic and, under the reaction conditions, inert and liquid. Depending on the reaction temperature, such suitable solvents or mixtures may be e.g. nitrile, such as acetonitrile, amides such as dimethyl formamide or dimethylacetamide, ethers such as ethylene glycol dimethyl ether, diethylene glycol dimethyl ether (diglymes), tetraethylene glycol dimethyl ether (tetraglymes), diethyl ether, diisopropyl ether, tetrahydrofurane, dioxane, furthermore sulfolane, esters such as ethyl acetate, or as well aromatic solvents such as nitrobenzene, fluorobenzene or chlorobenzene. It is also possible to use as solvents the reactants, especially the phosphorus compound II at a corresponding excess rate or the reaction products or the reaction mixture.

The quantity of solvent used is not of critical importance. Care has to be taken, however, that the reaction mixture can be mixed thoroughly at the chosen reaction temperature and that the viscosity does not rise too high, a possible proportion is for example 0.25 to 4 parts by volume of solvent(ml) per part by weight (g) of phosphorus compound II.

The process according to the invention can be carried out batchwise. Its continuous operation is also simple, of course, and may be carried through, for example, by continuous addition of the starting products I and II optionally together with a solvent into a reaction zone maintained at the reaction temperature, by withdrawing the reaction mixture after a suitable average residence time from this reaction zone and by possibly conveying this reaction mixture, in order to complete the reaction, to a supplementary reactor device.

The reaction products may be separated by simple distillation. Due to the fact that the perfluoralkoxy propionic acid fluoride which is obtained according to the process of the invention is hardly soluble in the simultaneously produced difluorophosphorane and in the equally used solvents, it is usually precipitating as heavier phase so that it can be removed from the reaction mixture. For purification's sake it is washed with a solvent, e.g. with acetonitrile, and distilled. The lighter difluorophosphorane is also purified by distillation, optionally after separation of the solvent.

When the operation is carried out with excessive hexafluoropropene epoxide or with a mixture containing hexafluoropropene, it is useful to heat the reaction mixture from 0° to 10° C prior to the separation of the reaction products, whereupon excessive hexafluoropropene epoxide and possibly hexafluoropropene escape as gases and may be recovered.

The obtained perfluoralkoxypropionic acid fluoride has the formula $C_9F_{16}O_4$ and a boiling point from 115° to 118° C. It contains one oxygen atom more and two fluorine atoms less than a trimeric hexafluoropropene epoxide. FIG. 1 illustrates its infrared spectrum. Its special feature is the marked IR adsorption at 9.7 microns (Perkin-Elmer 457, NaCl capillary), its structure corresponds to formula III - based on NMR spectroscopic analysis,

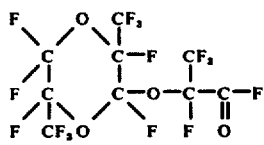

this formula III allowing for several conformation isomers and diasteromer variations, of course.

Additionally to the described perfluoralkoxypropionic acid fluoride the used phosphorus compound of formula II also yields an equivalent quantity of the corresponding dilfuorophosphorane of general formula IV

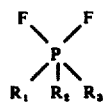

$R_1$, $R_2$ and $R_3$ have the meanings which have been indicated for compound II. These difluorophosphoranes are compounds known per se, but the manufacture of which was very complicated hitherto.

Starting from the structural formula III the novel perfluoralkoxypropionic acid fluoride is a perfluoro-α-[3,6-dimethyl-1,4-dioxanyl-2-oxy]-propionic acid fluoride. The total reaction may be represented by the following formula scheme:

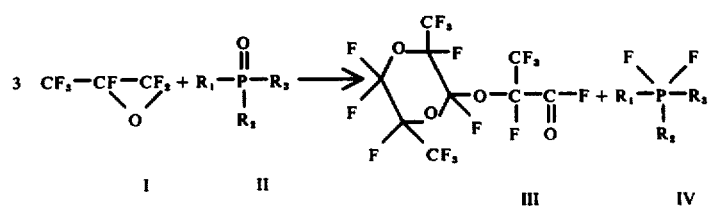

From said propionic acid fluoride an inert ethyl ether of the following formula is obtained by means of saponification and decarboxylizing in the presence of fluorine, in known manner,

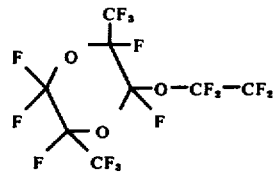

This perfluoro-2-ethoxy[3,6-dimethyl-1,4-dioxane] boils at from 101° to 104° C. The compound is suitable e.g. as lubricant, sealing liquid, heat transfer, isolation liquid or hydraulic liquid.

The following example and illustration explain the process according to the invention:

EXAMPLE 1

A solution of 300 ml of diethylene glycol dimethyl ether (diglyme) and 300 g (1.67 mole) of $PO[N(CH_3)_2]_3$ is introduced into a three-necked flask equipped with a high-efficiency cooler, agitator and a thermometer for measuring the cold. At temperatures of from −40° to −30° C 1400 g of a mixture of hexafluoropropene epoxide and hexafluoropropene (weight proportions 65 : 35) are metered in at the rate of 20 liters per hour, while agitating continuously. Subsequently stirring is continued for further 5 hours at the above mentioned temperature. Hexafluoropropene and excessive epoxide are then removed by slowly heating to 0° C, and the two-phased mixture is then separated in a separating funnel. The lower phase (871 g) is washed with 600 ml of acetonitrile and yields 777 g of a product mixture which is submitted to distillation.

| First fraction | 52–115° C | = | 57 g | |
|---|---|---|---|---|
| Second fraction | 115–118° C | = | 571 g | (72,0% theor. yield) |
| Third fraction | 118–170° C | = | 97 g | |
| Analysis of the second fraction | | C | F | H |
| $C_9F_{16}O_4$ | calc.: | 22.6 | 63.8 | 0 |
| | found: | 22.4 | 64.0 | >0.3 |

IR spectrum: adsorption at 9.7 microns (Perkin-Elmer 457, NaCl capillary)

The upper phase consists of a mixture of diglyme and difluoro-tri-dimethylaminophosphorane and is worked up by distillation. 257 g (89% of theoretical yield) of difluorotris-dimethylaminophosphorane are obtained; boiling point: 22° C at 0.4 mm/Hg.

| Analysis: | | C | H | F | N | P |
|---|---|---|---|---|---|---|
| $C_6H_{18}F_2NP$ | calc.: | 35.8 | 8.9 | 18.9 | 20.9 | 15.4 |
| | found: | 35.2 | 8.9 | 19.2 | 20.2 | 14.1 |

In case that the diglyme are replaced by tetraglyme, while maintaining the rest of the conditions unaltered, the result obtained is identical.

What is claimed is:
1. A perfluoro-α-[3,6-dimethyl-1,4-dioxanyl-2-oxy]-propionic acid fluoride of formula

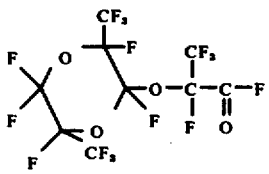

2. A perfluoro-2-ethoxy[3,6-dimethyl-1,4-dioxane] of the formula

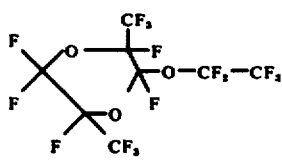

3. A process for the preparation of a perfluoralkoxy-propionic acid fluoride of the formula

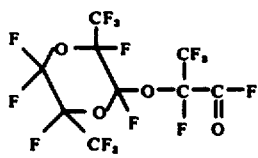

which comprises reacting hexafluoropropene oxide of the formula

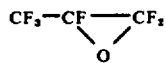

with a phosphoric acid tris-(dialkyl amide) of the formula

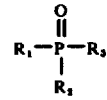

wherein $R_1$, $R_2$ and $R_3$ each represent a di-alkyl amine, the alkyl groups having from 1 to 4 carbon atoms, said reaction being carried out at a temperature of from $-50°$ C to $+10°$ C, and recovering said perfluoralkoxy-propionic acid fluoride.

4. The process of claim 3 wherein the reaction is carried out in the liquid phase.

5. The process of claim 3 wherein the reaction is carried out at a temperature of $-40°$ to $-25°$ C and at about normal pressure.

6. The process of claim 3 wherein the hexafluoropropene oxide is added to phosphoric acid tris-(dialkyl amide) at about $10°$ C and about the rate it is consumed and the reaction is carried out at about $-10°$ C and about normal pressure.

7. The process of claim 3 wherein the phosphorus compound is phosphoric acid tris-(dimethyl amide).

8. The process of claim 5 wherein about three moles of hexafluoro-propene oxide are added per mole of phosphorus compound.

* * * * *